United States Patent [19]

Saville

[11] Patent Number: Plant 5,957

[45] Date of Patent: Apr. 28, 1987

[54] ROSE PLANT NAMED SAVADI

[75] Inventor: F. Harmon Saville, Rowley, Mass.

[73] Assignee: Nor'East Miniature Roses, Inc., Rowley, Mass.

[21] Appl. No.: 775,023

[22] Filed: Sep. 11, 1985

[51] Int. Cl.[4] ..... A01H 5/00

[52] U.S. Cl. ..... Plt./7

[58] Field of Search ..... Plt./7

*Primary Examiner*—Robert E. Bagwill
*Attorney, Agent, or Firm*—Vincent G. Gioia

[57] ABSTRACT

A new miniature rose variety of orange red flower coloring but with varying color tones.

1 Drawing Figure

The present invention relates to a new and distinct variety of rose plant of the miniature rose class, which was originated by my crossing as seed parent the rose known as "Zorina" (U.S. Plant Pat. No. 2,321) and as pollen parent a seedling of my creation (unpatented) which is a cross of "Sheri Anne"×"Glenfiddich". The varietal denomination of this new variety is "Savadi".

Among the novel characteristics possessed by this new variety which distinguish it from its parents and all other varieties of which I am aware are its attractive well formed orange red colored flowers with varying orange red color tones and including some yellow-orange red blending but with more yellow toward point of petal attachment and pale pink blending on older outer petals. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "42A" is plate 42A of The Royal Horticultural Society Colour Chart.

Parentage: Seedling.
*Seed parent.*—"Zorina".
*Pollen parent.*—Seedling ("Sheri Anne"×"Glenfiddich").
Class: Miniature.

The following observations are made of specimens grown outdoors in Essex County, Mass., during the month of June.

FLOWER

Blooming habit: Continuous.

A. Bud:
(1) *Size.*—Medium.
(2) *Form.*—Pointed.
(3) *Color.*—When sepals divide — petal undersurface is first seen with relatively darker orange red tonality, near 42A, but with yellow shading toward point of petal attachment.
(4) *Sepals.*—Longer than bud, foliated.
(5) *Peduncle.*—Length — about 1 to 1¼ inches. Aspect — straight. Strength — erect. Color — near 144C.

B. Bloom:
(1) *Size.*—Average size when fully expanded — about 1¾ to 2 inches.
(2) *Borne.*—Singly.
(3) *Form.*—High centered at first, becoming flat, outer petals reflex to point and inner petals roll under upon opening.
(4) *Petalage.*—Number of petals under normal conditions — 20 to 25.
(5) *Color.*—After sepals fall and buds unfurl, flowers are a range of orange-red colors. Principal flower coloring is from near 42D to near 42A at its deepest tonality. However, shades lighter than 42D, including some pale pink tones on outer petals (near 56B through 56D), may also be seen. In addition some yellow coloring is visible at lower petal segments on both petal top and undersurfaces toward point of attachment. Yellow and orange tones seem to blend together. Deeper orange red tonality appears at flower centers.

C. Petals:
(1) *Texture.*—Thick.
(2) *Appearance.*—Inside — velvety, outside — satiny.
(3) *Form.*—Broad, fan shaped.
(4) *Arrangement.*—Regularly arranged, imbricated.
(5) *Petaloids in center.*—Few.
(6) *Persistence.*—Drop off cleanly.
(7) *Fragrance.*—Slight.
(8) *Lasting quality.*—Long lasting as cut flower.

REPRODUCTIVE ORGANS

A. Stamens, filaments and anthers:
(1) *Arrangement.*—Regularly arranged around styles.
(2) *Color.*—Near 28A.

B. Pollen:
*Color.*—Near 28A.

C. Styles: Even length, short.

D. Stigmas:
*Color.*—Near 154C.

E. Hips: None observed.

PLANT

A. Form: Compact, upright.

B. Growth: Vigorous, uniform branching.
*Height attained.*—About 14 to 16 inches.

C. Foliage: Compound 5 to 7 leaflets.
(1) *Size.*—Medium.
(2) *Quantity.*—Abundant.
(3) *Color.*—New foliage: Upper side — near to 147B. Under side — near to 138B. Old foliage: Upper side — near 147B. Under side — near 138B.
(4) *Shape.*—Oval, pointed.
(5) *Texture.*—Upper side is semi-glossy and under side is matte.
(6) *Edge.*—Serrated.
(7) *Serration.*—Serrate.
(8) *Leaf stem.*—Color — near 144B. Under side — near 144C.
(9) *Stipules.*—Medium, slightly bearded.
(10) *Resistance to disease.*—Blackspot — average. Mildew — average. Rust — average.

D. Wood:
(1) *New wood.*—Color — near 144B. Bark — smooth.
(2) *Old wood.*—Color — near 141C. Bark — rough.

E. Thorns:
(1) *Thorns.*—Quantity (main stalk) — ordinary. On laterals from stalk — few to none. Form — long, thin, pointed. Length — medium. Color — near 182C. Position — irregular.
(2) *Prickles.*—None.

F. Winter hardiness: Requires ordinary protection in extreme climates.

I claim:

1. A new and distinct variety of rose plant of the miniature rose class, substantially as shown and described, characterized particularly by good form and unusual orange red colored flowers of varying orange red tones but including some yellow-orange red blending toward point of petal attachment and pale pink blending on older outer petals.

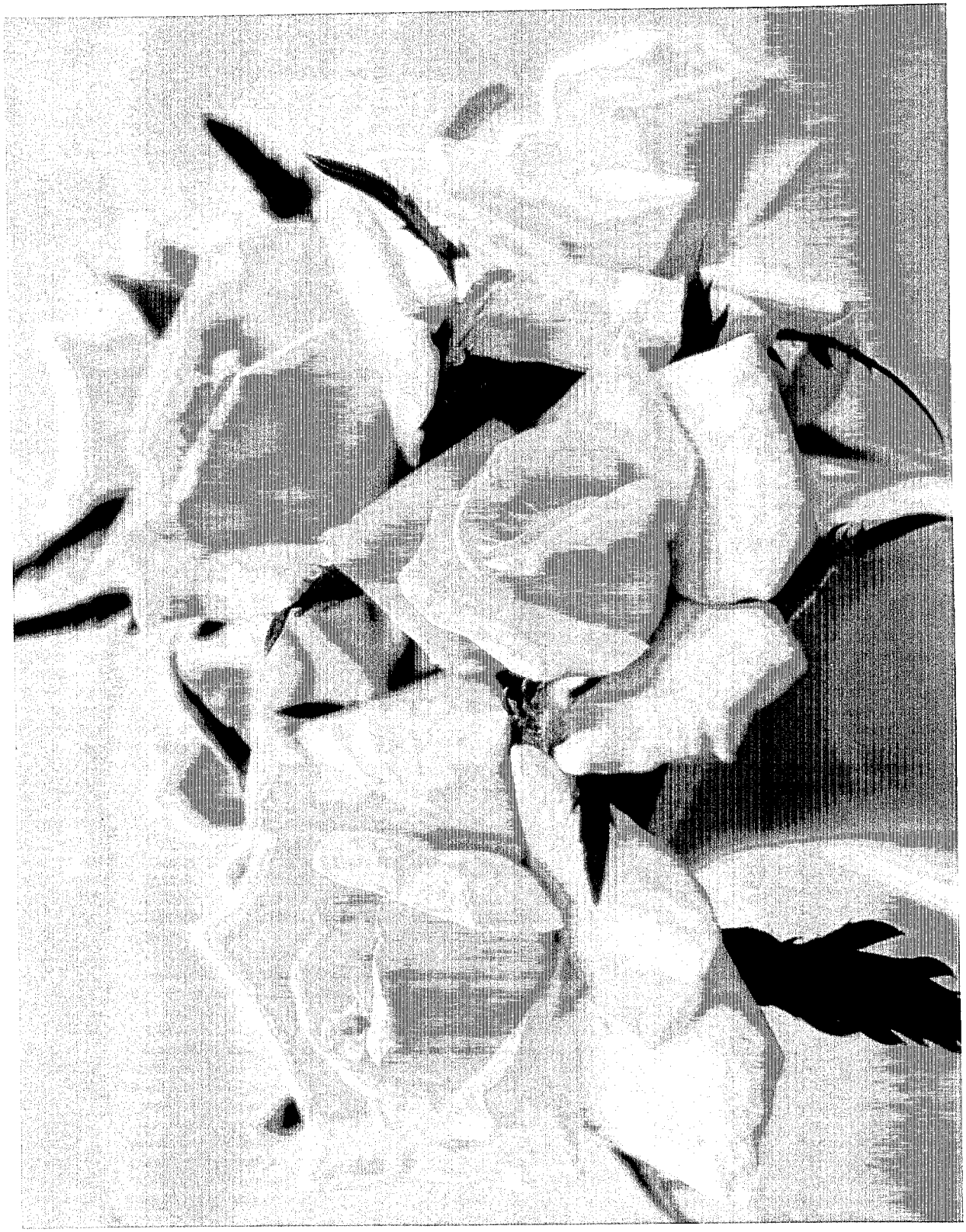

* * * * *